(12) United States Patent
Shukla et al.

(10) Patent No.: US 8,636,636 B2
(45) Date of Patent: Jan. 28, 2014

(54) GRID RADIOTHERAPY FOR STATIC AND DYNAMIC TREATMENT DELIVERY

(75) Inventors: Himanshu P. Shukla, Lafayette, CA (US); Walter A. Aguilar, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 401 days.

(21) Appl. No.: 13/016,768

(22) Filed: Jan. 28, 2011

(65) Prior Publication Data

US 2012/0197058 A1    Aug. 2, 2012

(51) Int. Cl.
*A61N 5/00* (2006.01)
(52) U.S. Cl.
USPC .................................................. 600/1
(58) Field of Classification Search
USPC .............. 600/1, 2, 425; 378/64, 98.11, 98.12, 378/163, 164
See application file for complete search history.

(56) References Cited

U.S. PATENT DOCUMENTS

2007/0239145 A1* 10/2007 Laderman ..................... 606/9
2010/0320402 A1   12/2010 Ahmed et al.

OTHER PUBLICATIONS

Robert D. Zwicker, et al., "Therapeutic Advantage of Grid Irradiation for Large Single Fractions", Int. J. Radiation Oncology Biol. Phys., vol. 58, No. 4, 2004, Copyright © 2004, Elsevier Inc., (pp. 1309-1315, total 7 pages).
Mohammed Mohiuddin et al., "High-Dose Spatially-Fractionated Radiation (GRID): A New Paradigm in the Management of Advanced Cancers", Int. J. Radiation Oncology Biol. Phys., vol. 45, No. 3, 1999, Copyright © 1999, Elsevier Science Inc., (pp. 721-727, total 7 pages).
A. S. Meigooni et al., "Dosimetric Characteristics with Spatial Fractionation Using Electron Grid Therapy", Medical Dosimetry, vol. 27, No. 1, 2002, Copyright © 2002 American Association of Medical Dosimetrists, PII: S0958-3947(02)00086-9, (pp. 37-42, total 6 pages).
Sotirios Stathakis et al, "Dosimetric evaluation of multi-pattern spatially fractionated radiation therapy using a multi-leaf collimator and collapsed cone convolution superposition dose calculation algorithm", Department of Radiation Oncology, Applied Radiation and Isotopes 67 (2009), (pp. 1939-1944, total 6 pages).

* cited by examiner

*Primary Examiner* — Christine Matthews
*Assistant Examiner* — Joshua D Lannu

(57) ABSTRACT

Some aspects include a system, method, and computer-readable medium to divide a representation of a target volume into an array of sub-volumes; define a high dose volume to which a high dose of radiation is to be delivered; define a plurality of sampling volumes; direct an estimated dose of radiation to each sub-volume; determine whether the dose of radiation delivered to each high dose volume is at least a minimum threshold dose, and that the radiation delivered to the plurality of sampling volumes for each of the sub-volumes is at least a minimum difference less than the radiation delivered to the high dose volume; adjust the estimated dose of radiation directed to each sub-volume; and develop a radiation treatment plan, including the adjusted dose, to invoke a biological effect of spatially separated radiation.

13 Claims, 9 Drawing Sheets

200

```
┌─────────────────────────────────────────────────────┐
│  DIVIDE A REPRESENTATION OF A TARGET VOLUME INTO    │
│  AN ARRAY OF SUB-VOLUMES                       205  │
└─────────────────────────────────────────────────────┘
                          │
                          ▼
┌─────────────────────────────────────────────────────┐
│  DEFINE, FOR EACH SUB-VOLUME, A HIGH DOSE VOLUME TO │
│  WHICH A HIGH DOSE OF RADIATION IS TO BE DELIVERED  │
│                                                210  │
└─────────────────────────────────────────────────────┘
                          │
                          ▼
┌─────────────────────────────────────────────────────┐
│  DEFINE, FOR EACH SUB-VOLUME, A PLURALITY OF SAMPLING│
│  VOLUMES, THE SAMPLING VOLUMES BEING SMALLER THAN THE│
│  HIGH DOSE VOLUME OF EACH SUB-VOLUME           215  │
└─────────────────────────────────────────────────────┘
                          │
                          ▼
┌─────────────────────────────────────────────────────┐
│  DIRECT AN ESTIMATED DOSE OF RADIATION TO EACH SUB-VOLUME│
│                                                220  │
└─────────────────────────────────────────────────────┘
                          │
                          ▼
┌─────────────────────────────────────────────────────┐
│  DETERMINE WHETHER THE DOSE OF RADIATION DELIVERED TO│
│  EACH HIGH DOSE VOLUME SATISFIES THE SPATIALLY      │
│  SEPARATED RADIATION CRITERIA                  225  │
└─────────────────────────────────────────────────────┘
                          │
                          ▼
┌─────────────────────────────────────────────────────┐
│  ADJUST THE ESTIMATED DOSE OF RADIATION DIRECTED TO │
│  EACH SUB-VOLUME UNTIL THE SPATIALLY SEPARATED      │
│  RADIATION CRITERIA ARE SATISFIED              230  │
└─────────────────────────────────────────────────────┘
                          │
                          ▼
┌─────────────────────────────────────────────────────┐
│  DEVELOP A RADIATION TREATMENT PLAN, INCLUDING THE  │
│  ADJUSTED DOSE, TO INVOKE A BIOLOGICAL EFFECT OF    │
│  SPATIALLY SEPARATED RADIATION                 235  │
└─────────────────────────────────────────────────────┘
```

*FIG. 2*

GRID RADIOTHERAPY FOR STATIC AND DYNAMIC TREATMENT DELIVERY

BACKGROUND

1. Field

The embodiments described below relate generally to radiotherapy treatment. More specifically, some embodiments are directed to determining radiotherapy treatment plan to invoke a biological effect of spatially separated radiation.

2. Description

Radiotherapy or radiation therapy is used to treat cancer and other diseases with ionizing radiation. Conventional radiotherapy systems generate and direct a beam of radiation to a targeted treatment volume within a patient. The radiation beam is intended to injure or destroy cells within the target volume by causing ionizations within the cells or other radiation-induced cell damage.

Radiotherapy treatment plans for delivering radiation to a patient are intended to maximize radiation delivered to a target area, while minimizing the radiation delivered to surrounding healthy tissue. In this regard, a number of different techniques have been developed to address different target areas and types of tumors, as well as radiation exposure concerns. Grid radiotherapy or spatially separated radiotherapy traditionally attaches a grid collimator to the gantry of a radiotherapy device. The grid collimator can produce beneficial biological effects by splitting a radiation beam into a number of smaller beams, shielding portions of a target from being irradiated, and producing a non-uniform irradiation pattern. It has been observed that the biological effects of grid therapy are largely insensitive to changes in dimensions and regularity of the openings in the grid collimator. However, the biological effects of grid radiotherapy may be sensitive to a maximum dose delivered to a volume.

In some instances, a beam shaping device such as a multi-leaf collimator (MLC) may be used to emulate a physical grid collimator, in an effort to achieve the biological benefits of grid radiotherapy but without the need for the physical grid block. However, the emulating of the physical grid collimator constrains prior MLC radiotherapy techniques by simulating the radiation delivery patterns achieved by the conventional physical grids.

The present inventors have realized that conventional grid radiation therapy is limited by physical grid devices, undesired levels of radiation exposure to patients, and other inefficiencies related to emulating patterned grids and MLC grid radiotherapy is also limited due to constraints associated with emulating a physical grid. Accordingly, methods and systems to provide a dynamic delivery of radiation treatment by a radiotherapy system are desired.

SUMMARY

In order to address the foregoing, some embodiments provide a system, method, apparatus, and medium to divide a representation of a target volume into an array of sub-volumes; define a high dose volume to which a high dose of radiation is to be delivered; define a plurality of sampling volumes; direct an estimated dose of radiation to each sub-volume; determine whether the dose of radiation delivered to each high dose volume is at least a minimum threshold dose, and that the radiation delivered to the plurality of sampling volumes for each of the sub-volumes is at least a minimum difference less than the radiation delivered to the high dose volume; adjust the estimated dose of radiation directed to each sub-volume; and develop a radiation treatment plan, including the adjusted dose, to invoke a biological effect of spatially separated radiation.

In some embodiments, a method, system, and medium herein may include administering and delivering radiation treatment to a target volume using the treatment plans disclosed herein to invoke a biological effect of spatially separated radiation.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein:

FIG. 2 is a flow diagram of a process, according to some embodiments;

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

In an effort to provide a system, method, apparatus, and medium for determining and providing a radiation treatment plan that includes an adjusted dose to invoke a biological effect of spatially separated radiation, a radiation treatment plan may be developed that seeks to emulate biological effects of spatially separated or grid radiation that considers, as a primary objective, various constraints to invoke the biological effects of spatially separated radiation. Moreover, the goal of invoking the biological effects of spatially separated radiation herein may not be primarily achieved by emulating the grid-like regularity beam distribution of conventional grid radiation therapy. Instead, some embodiments herein determine dose delivery parameters, including related spatial parameters that invoke the biological effects of spatially separated radiation.

In some embodiments, the biological effects of spatially separated radiation may include loco-regional vascular destruction of irradiated areas and the induction of cell death of cancer cell by signals from adjacent irradiated cancer cells—the "bystander" effect. Other observed biological effects may also be achieved by spatially separated radiation. For example, it has been observed that the conventional spatially separated radiation therapy is sensitive to a maximum dose delivered to a volume, in contrast to the observed relative insensitivity over a range of grid dimensions and regularity. As such, some of these and other biological effects are achievement goals of some of the processes and systems herein.

In some embodiments, a biological effect and optimization of same, may be achieved by a transformation of a physical dose distribution into a biologic metric. In some instances, one or more models may be developed to effectuate such transformations. In some embodiments, an ensemble of physical doses may be considered, wherein a transformation provides a framework that determines and considers probabilities of various biological effects.

In some embodiments herein, physical constraints may be considered to achieve the desired biological effect of spatially separated radiation and the optimization thereof. In some instances, a number of novel concepts contribute to the effort of achieving the goal of obtaining the desired biological effects of spatially separated radiation. Some concepts regarding methods and systems to achieve the desired biological effect of spatially separated radiation and the optimization thereof will be discussed with reference to a target volume to be treated by radiotherapy radiation.

Figure 1:
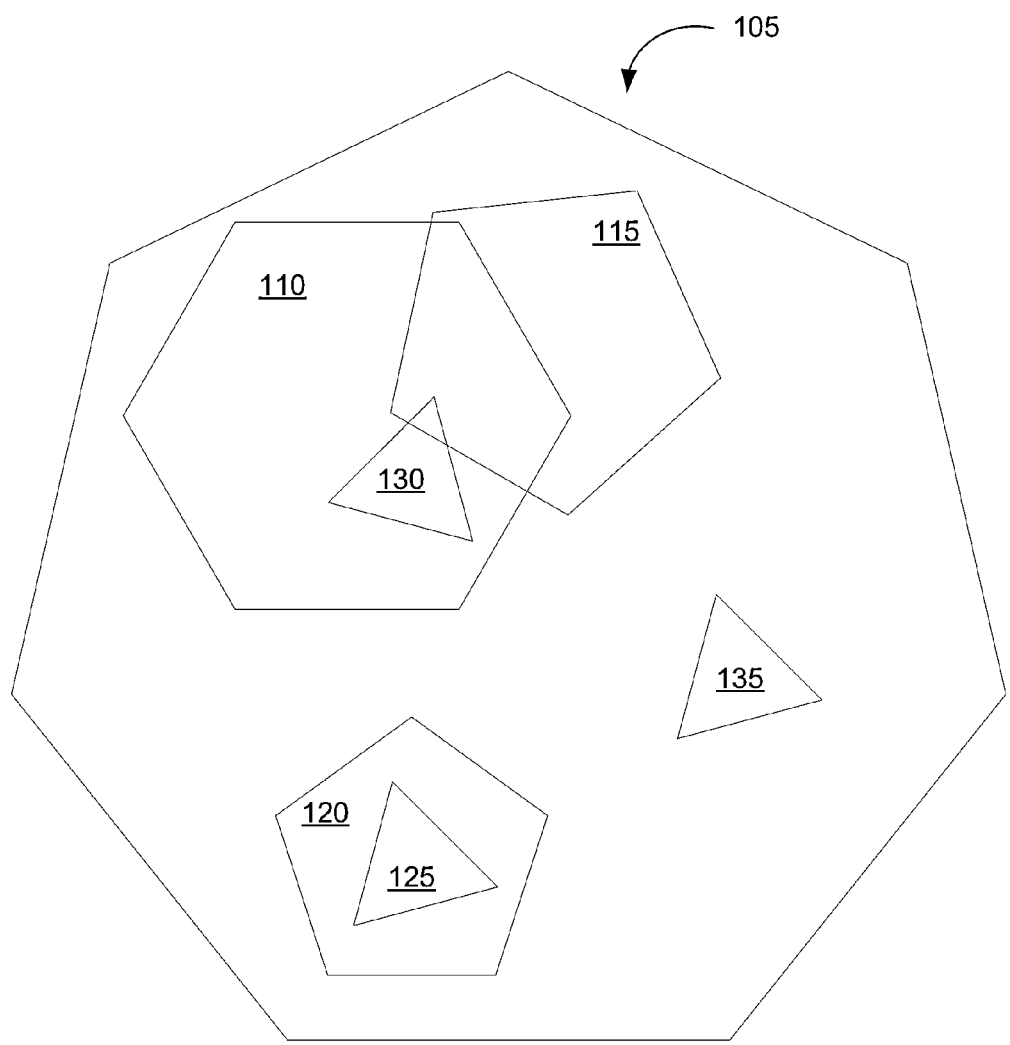
FIG. 1 is an illustrative depiction of a target volume, according to some embodiments.

FIG. 1 is an illustrative depiction of a target volume 100. Target volume 100 may, for treatment planning purposes, be a representative model of an area or volume of a patient that may be treated with radiotherapy radiation. Target 100 has a number of sub-volumes or sub-divisions therein, including sub-volumes 110-135. In the example of FIG. 1, sub-volume 110 has a first size (A), sub-volumes 115 and 120 have a second size (B), and sub-volumes 125, 130, and 135 have a third size (C). It is noted the target volume 105 is about 1 to 4 orders of magnitude larger than any of the sub-volumes. In the present example, several of the sub-volumes have the same or similar size. However, this may not be a necessary requirement.

For FIG. 1 and the sized sub-volumes therein, sub-volume 110 is larger than sub-volumes 115, 120 that are larger than sub-volumes 125, 130, 130. That is, A>B>C. In some embodiments, the configuration parameters for a beam shaping device of a radiotherapy device to invoke a biological effect comparable to spatially separated radiation therapy may be based on a physical constraint. The physical constraint may relate to a desire to have a large dose differentials within a target volume. A large dose differential is known (i.e., has been demonstrated) to be a characteristic of effective spatially separated radiation therapy. As such, the physical constraint of a large dose differential within a target volume may provide the desired biological results when coupled with the burst mode radiation delivery herein.

In some embodiments, a dose differential is the difference between a maximum dose delivered to a target volume minus a minimum dose delivered to that target. In some instances, the maximum dose delivered may be 100% (no blockage or attenuation of the radiation) and the minimum dose delivered is a lesser percentage than full radiation. In some embodiments, there may be a minimum dose differential required for a target volume of a given size to achieve desired biological effects. In this manner, setting and adhering to a physical constraint for the dose differential in target volume of a given size may provide a mechanism to obtain desired biological effects.

In accordance with spatially separated radiation where an underlying goal of the grid is to have both a very high dose and a very low dose within a sub-volume to achieve biological effects, a constraint for achieving desired biological effects will similarly dictate large dose fluctuations within a target volume. The larger the sub-volume, the larger the dose differential between the maximum dose and the minimum dose that must be achieved. This constraint may be used in determining the treatment plan and other control instructions. Accordingly, for sub-volumes 110-135, where 110 (A)>115, 120 (B)>125, 130, 135 (C) and $\Delta Dose \equiv |Dose\ Maximum - Dose\ Minimum|$; a sample constraint may include $\Delta Dose_{110} > \Delta Dose_{115, 120} > \Delta Dose_{125, 130, 135}$. In this example, $\Delta Dose$ refers to the dose differential within the sub-volume.

It should be appreciated that it need not be necessary nor true that an arbitrary sub-volume A in location X must have a larger $\Delta Dose$ than a smaller sub-volume located at a completely arbitrary position Y, especially if the smaller sub-volume is not completely contained by A.

Optimization of the biological effects may entail tuning the configuration parameters for the beam shaping device. The tuning of the configuration parameters for the beam shaping device may involve an iterative process where prior biological effects are analyzed and adjustments are made to the configuration parameters for the beam shaping device in an effort to increase the biological effects realized by the radiation treatment herein.

Figure 3:
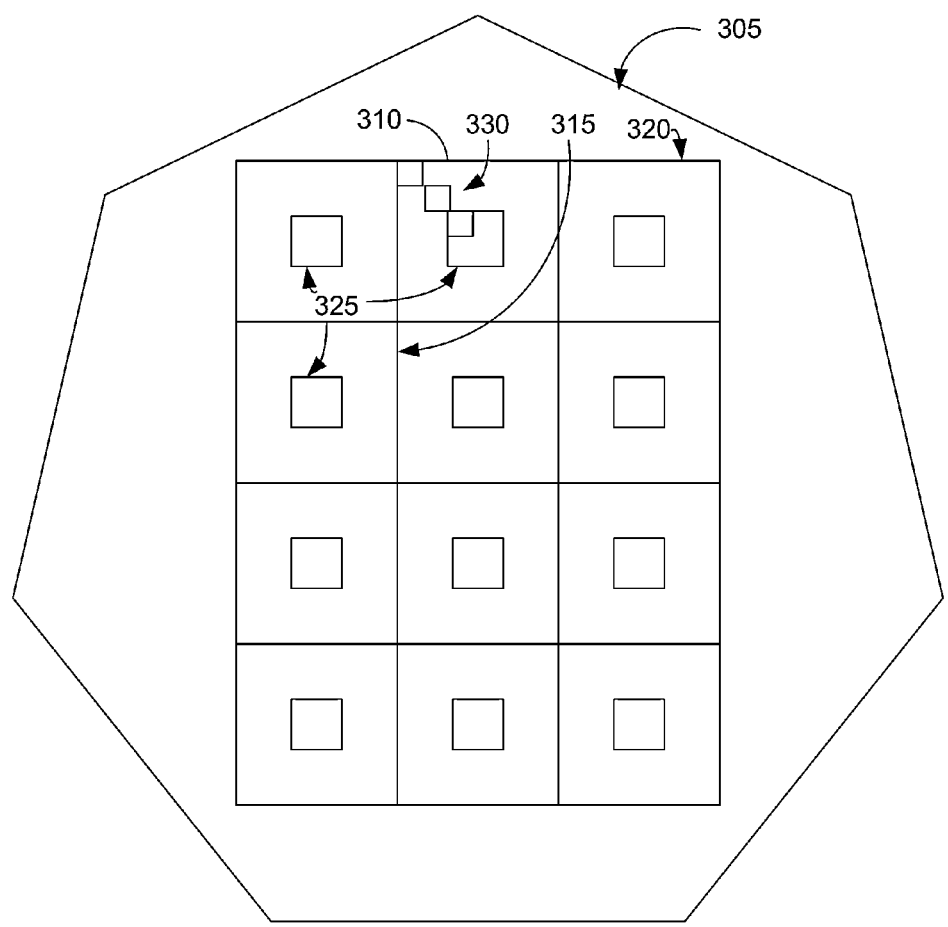
FIG. 3 is an illustrative depiction of a target volume, divided according to some embodiments.

A process for determining a treatment plan herein may generally include the flow of process 200 shown in FIG. 2. As illustrated, operation 205 includes dividing a representation of a target volume into an array of sub-volumes. The shape, configuration, and size of the sub-volumes may vary as illustrated in FIG. 1. However, since the dimensions and configurations of the sub-volumes may have to be determined, calculated, and/or stored, some embodiments (including but not limited to some practical embodiments) may include sub-volumes that are substantially regularly sized and spaced, as shown in FIG. 3. It is emphasized that the regular spacing and sizing, at least initially in process 200, is not a requirement or constraint on process 200. In some embodiments, the sub-volumes are spaced apart within a pre-determined minimum distance of about 1 centimeter to about a maximum of about 5 centimeters.

In FIG. 3, target volume 305 is divided into an array of sub-volumes. Some of the sub-volumes include representative sub-volumes 310, 315, and 320. For purposes of clarity, not all of the sub-volumes of target volume 305 are individually referenced by reference numerals. The sub-volumes are made to provide a context for the sampling of high doses and low doses since a underlying goal of spatially separated radiation is the occurrence of both a very high dose and a very low dose within a sub-volume of the target volume. In some embodiments, each sub-volume occupies about 0.1% to about 10% of the target volume.

According to operation 210 of FIG. 2, a high dose volume is defined for each sub-volume. The high dose volume is a volume within each sub-volume to which a high dose of radiation is to be delivered, in accordance with the desired goal of having a very high dose within the sub-volumes.

FIG. 3 further illustrates a number of high dose volumes located within the sub-volumes of target volume 305. In some embodiments, the high dose volumes may be centrally located within their associated sub-volume. The example of FIG. 3 illustrates this aspect of centrally located high dose volumes, as defined for each sub-volume. Some, but not all, of the high dose volumes are referenced so as not to obscure the drawing. The particularly referenced high dose volumes include high dose volumes 325, each located within a separate, distinct sub-volume. In some embodiments, a high dose volume (e.g., 325) may be on the order of about 5% to 20% of an associated sub-volume (e.g., 310).

It is noted that the high dose volumes defined by some embodiments herein need not be centrally located within a sub-volume. In some instances, treatment plan development and optimization aspects may use centrally located high dose volumes for planning and optimizing purposes, at least in some phase thereof. However, the high dose volumes do not, as a rule, need to be centrally located within a sub-volume. It may be that the results of a treatment plan development and/or optimization suggest or recommend that one or more high dose volumes be located centrally within a sub-volume.

Returning to process 200 of FIG. 2, a plurality of sampling volumes may be defined for each of the sub-volumes. Each of the plurality of sampling volumes is defined as being smaller than the high dose volume of the same, associated sub-volume. As referred to herein, sampling volumes are volumes for which samples of a delivered dose of radiation will be obtained. Ideally, as many dose samples within each sub-volume surrounding each high dose volume will be taken, in an effort to detect and characterize the (very) low dose region with each sub-volume. In some embodiments, each sampling volume may be about 1% to about 10% of the sub-volume associated therewith.

Continuing with the development and optimization of a spatially separated radiation treatment plan at 220, process 200 of FIG. 2 directs an estimated dose of radiation to each sub-volume. The estimated dose may be based on a calculation specific to a particular patient or based on a broader sampling. In some embodiments, either prior to or part of operation 220, a radiotherapy device, system, or apparatus may be programmed, controlled, or configured to calculate and deliver radiation in accordance herewith. For example, in some embodiments, an operation (not shown) prior to operation 220 may include a process to load electromechanical radiation therapy machine settings necessary for dose calculation.

At 225, a determination is made whether the dose of radiation delivered to each high dose volume is at least a minimum threshold dose, and whether the radiation delivered to the plurality of sampling volumes for each of the sub-volumes is at least a minimum difference less than the radiation delivered to the high dose volume. These constraints may be used to achieve the desired biological effects of spatially separated radiation therapy. The sampling volumes discussed herein are used in taking the sample measurements for the determination of 225.

In some embodiments, the minimum threshold dose of radiation is about 70% to about 90% of the estimated maximum dose of radiation. In some embodiments, this range of values reduces to an optimal value of no less than about 85%. However, other ranges of values may legitimately occur due to a specific target volume, patient, etc.

In some embodiments, the minimum difference is about 50% to about 60% below the high dose of radiation directed to the sub-volume. Accordingly, if the high dose delivered is 90% and the minimum difference below that is about 50% to about 60%, then the low or minimum dose will be in the range of about 40% to about 30%. In some embodiments, a range of about 20% to about 30% is a goal for a low dose within a sub-volume. Thus, a difference of about 60% to about 70% may be a desired difference (though not a minimum).

In an effort to optimize the spatially separated treatment plan herein, operation 230 includes adjusting the estimated dose of radiation directed to each sub-volume until the radiation delivered to each high dose volume is at least a minimum threshold dose, and the radiation delivered to the plurality of sampling volumes for each of the sub-volumes outside of the high dose volume is at least a minimum difference less than the radiation delivered to the high dose volume. Process 200 may therefore include an iterative flow between operations 220 and 230 until the estimated dose of radiation directed to each sub-volume until the radiation delivered to each high dose volume is at least a minimum threshold dose, and the radiation delivered to the plurality of sampling volumes for each of the sub-volumes is at least a minimum difference less than the radiation delivered to the high dose volume.

In some embodiments, further conditions and criteria may be considered in the adjusting operation 230. As an example, adjusting operation 230 may include altering or changing a spatial relationship between the high dose volumes, the sampling volumes, and the sub-volumes. For example, the size, shape, and orientation of the high dose volumes, the sampling volumes, and the sub-volumes may be changed.

Figure 4:
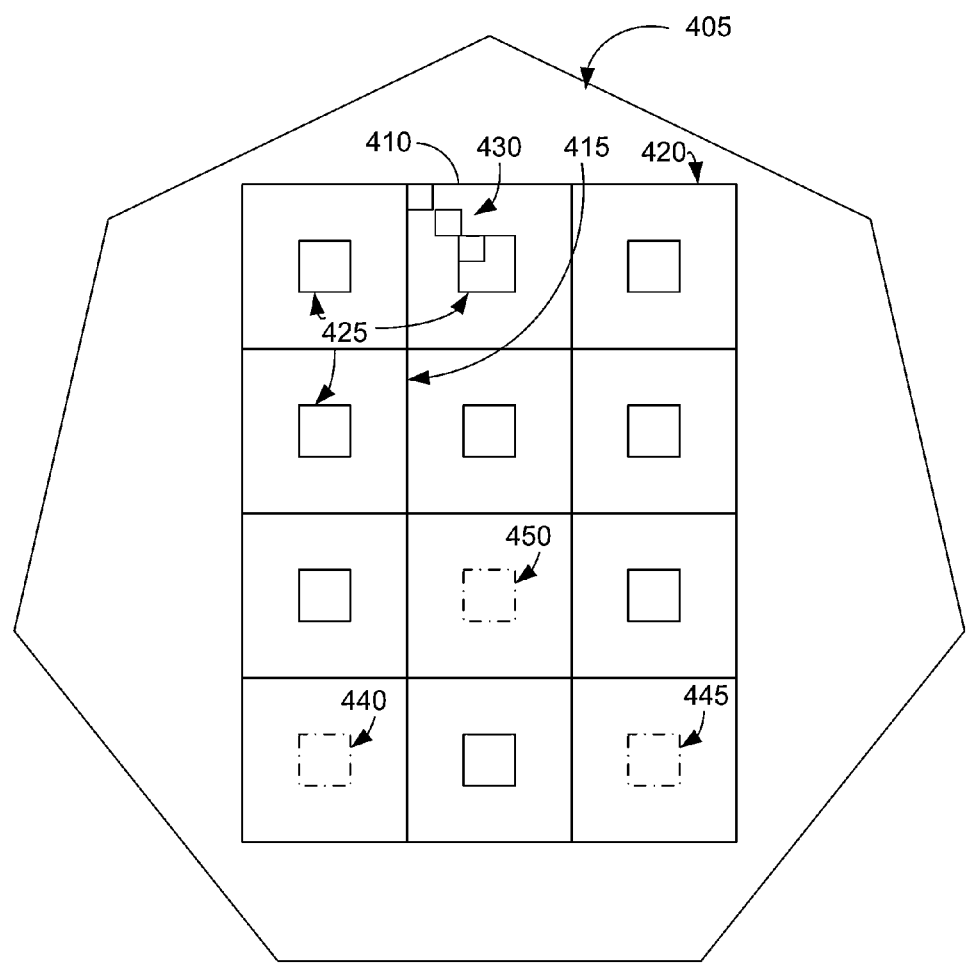
FIG. 4 is an illustrative depiction of a target volume, according to some embodiments.

In some embodiments, the adjusting of operation 230 may include lowering the estimated dose delivered to at least some of the sub-volumes. FIG. 4 provides an illustrative depiction of a target volume 405 including sub-volumes (e.g., 410, 415, and 420); high dose volumes (e.g., 425); and sampling volumes (e.g., 430). Notably, high dose volumes 440, 445, and 450 have had the dose delivered thereto lowered, in an effort to achieve the desired high dose, surrounded by the desired low dose, within the greatest number of sub-volumes for target volume 405.

Figure 5:
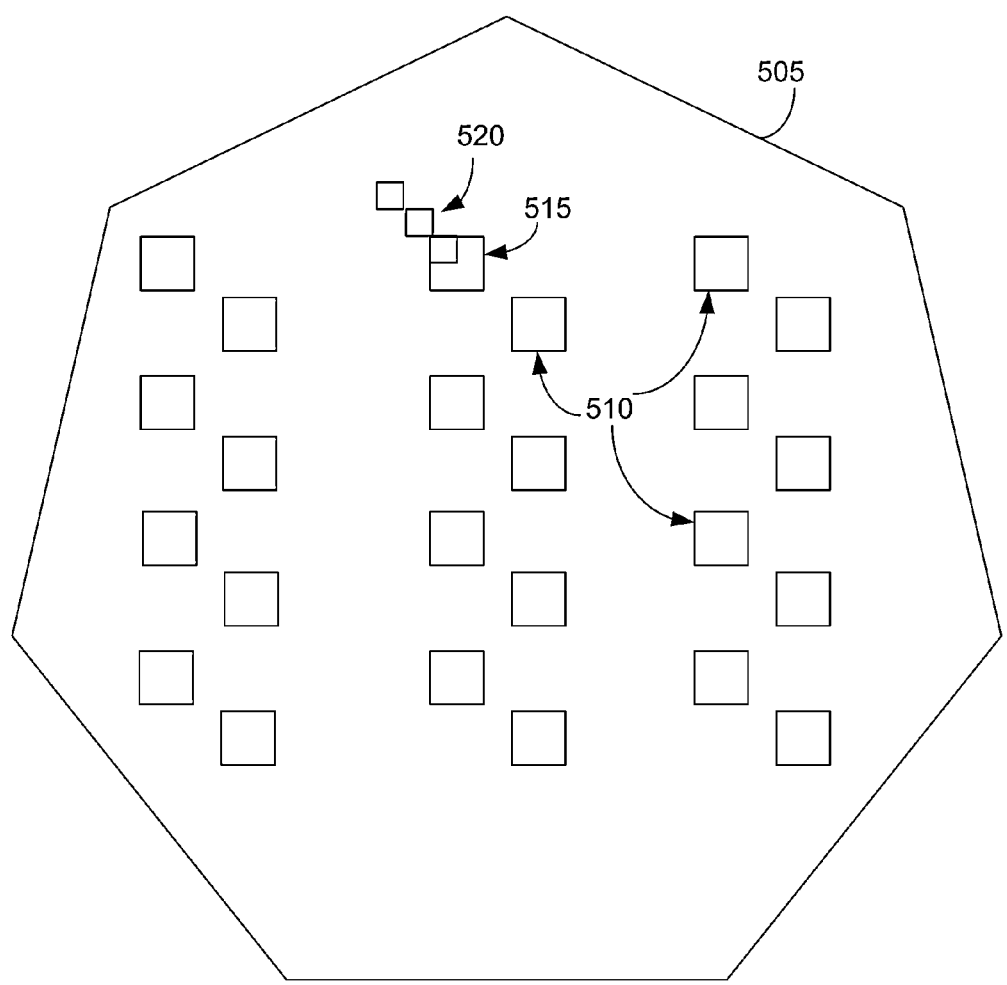
FIG. 5 is an illustrative depiction of a target volume, according to some embodiments.

FIG. 5 is an illustrative example of a target volume including another sub-volume arrangement. Here, the high dose volumes (e.g., 510, 515) and/or dose sampling volumes (e.g., 520) may be anisotropic and adaptive in nature. Process 200 may consider more flexible aspects of packing high dose regions with low dose surroundings. These considerations operate to also achieve the goal of having a delivered high dose and a delivered low dose (relative to a maximum administered dose) within every (small) sub-volume.

In some embodiments, process 200 may consider the biological effect of the radiation distribution. This distribution consideration may be an alternative to the maximum and minimum goals of physical dose in some instances, and one of multiple considerations in other embodiments.

Process 200 proceeds to operation 235, where a radiation treatment plan, including the adjusted dose to invoke a biological effect of spatially separated radiation is developed. This thus developed treatment plan may be referred to herein as a spatially separated radiation or grid radiation treatment plan. The may be administered and delivered by any radiotherapy device and system, now known or that becomes known in the future.

Figure 6:
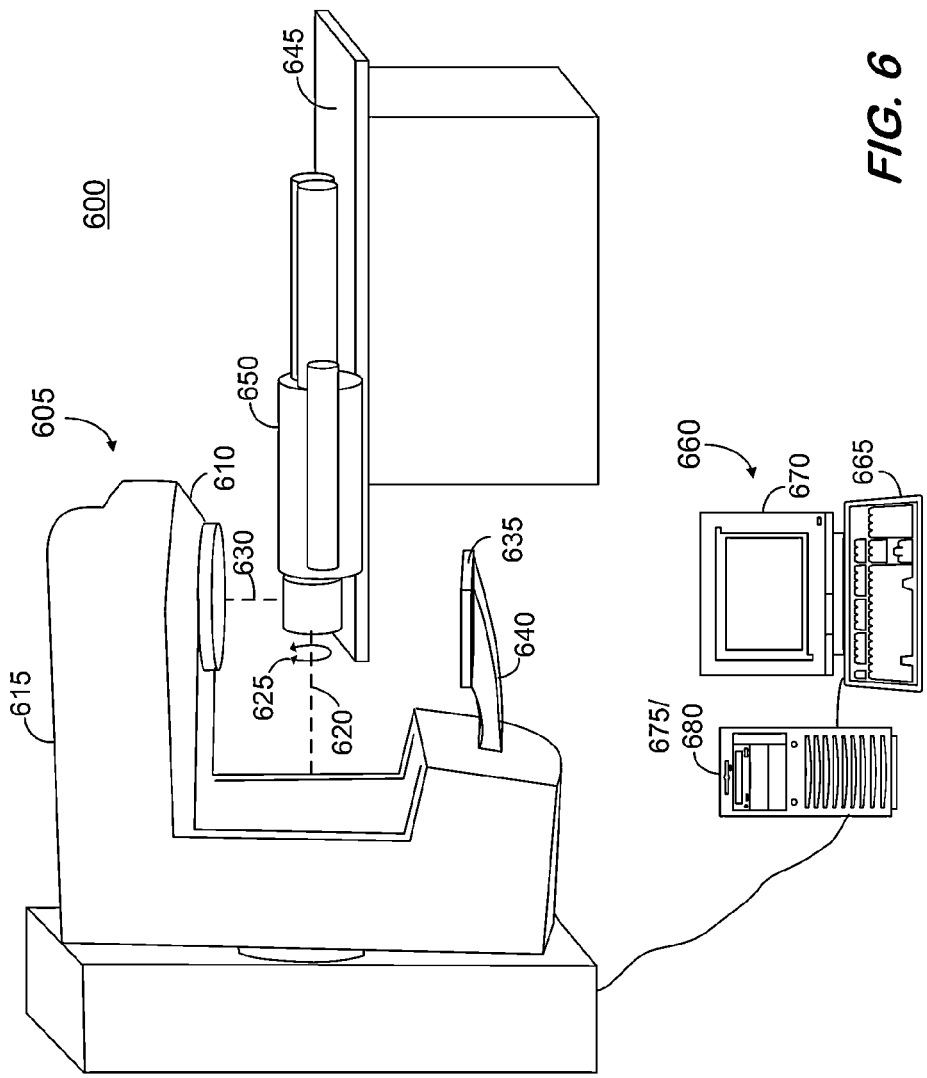
FIG. 6 is a perspective view of a treatment room according to some embodiments.

The spatially separated treatment plan(s) developed and optimized herein may be administered delivered by any of a number of systems and radiotherapy protocols. FIG. 6 illustrates radiotherapy treatment room 600 pursuant to some embodiments. Radiotherapy treatment room 600 includes linear accelerator (linac) 605, table 645 and operator console 660. The various components of radiotherapy treatment room 600 may be used to deliver a beam of radiation to an object such as patient 650. The patient may be positioned to receive the beam according to a radiation treatment plan. The elements of treatment room 600 may be employed in other applications according to some embodiments.

Linac 605 generates and emits a radiation beam (e.g., an x-ray beam) from treatment head 610. The radiation beam may comprise electron, photon or any other type of radiation. According to some embodiments, the beam exhibits energies in the megavoltage range (i.e. >1 MeV) and may therefore be referred to as megavoltage beam. In some embodiments, LINAC 105 may emit a radiation beam in relatively short bursts of time with a relatively high intensity. As an example, high intensity may refer to 10 GY/min and higher, where 20 Gy/min is typical, although higher intensities may be used. In some embodiments, a typical burst time duration may be about (0.5-2.0) seconds, although in some embodiments it may be longer or shorter.

Treatment head 610 is coupled to a projection of gantry 615. Gantry 615 is controllable to be rotatable around gantry axis 620. As indicated by arrow 625, gantry 615 may rotate clockwise or counter-clockwise according to some embodiments. Rotation of gantry 615 serves to rotate treatment head 610 around axis 620. Gantry 615 may also, in some aspects, be moveable in other directions other than or in addition to that indicated by arrow 625.

During radiation emissions (e.g., treatment, imaging, calibration, and other procedures) treatment head 610 emits a divergent beam of megavoltage x-rays along beam axis 630. The beam is emitted towards the isocenter of linac 605. The isocenter may be located at the intersection of beam axis 630 and gantry axis 620. Due to divergence of the beam and the shaping of the beam by beam-shaping devices in treatment head 610, the beam may deliver radiation to a volume of patient 650 rather than only through the isocenter.

Table 645 may support a patient during radiation treatment and other aspects discussed herein. Table 645 may be adjustable to assist in positioning patient 650 or a particular target area and volume of the patient at the isocenter. Table 645 may also be used to support devices used for such positioning, for calibration and/or for verification. In some embodiments, table 645 may be selectively moved during at least portions of a radiation treatment, in accordance with a treatment plan.

Imaging device 635 may comprise any system to acquire an image based on radiation received at the imaging device. Imaging device 635 may be attached to gantry 615 in any manner, including an extendible and retractable (i.e., moveable) housing 640. Rotation of gantry 615 may cause treatment head 610 and imaging device 635 to rotate around the isocenter such that the isocenter remains located between treatment head 610 and imaging device 635 throughout stationary and rotational movements of gantry 615.

Imaging device 635 may acquire projection images before, during and/or after radiation treatment. In some embodiments, imaging device 635 may include an analog or a digital radiation detector. Imaging device 635 may be used to acquire images based on radiation emitted from treatment head 610. These images may reflect the attenuative properties of objects located between treatment head 610 and imaging device 635. Such projection images may be used to determine imaging geometry parameters associated with the imaging system comprising treatment head 610 and imaging device 635. The two-dimensional projection images and/or three-dimensional images reconstructed based on the projection images may be used to detect, monitor, and record a target area or volume (e.g., a tumor) position and a movement of the target area or volume.

Operator console 660 includes input device 665 for receiving instructions from an operator such as an instruction to calibrate linear accelerator 105 and an instruction to configure the beam shaping device of treatment head 610 (e.g., a collimator) with a particular field of view for a particular interval of time. Console 660 also includes output device 670 that may include a monitor for presenting acquired three-dimensional images, operational parameters of linear accelerator 605 and/or interfaces for controlling elements thereof. Input device 665 and output device 670 are coupled to processor 675 and storage 680.

Processor 675 executes program code according to some embodiments. The program code may be executable to control linear accelerator 605 to operate as described in various methods and processes herein. The program code may be stored in storage 680, which may comprise one or more storage media of identical or different types, including but not limited to a fixed disk, a floppy disk, a CD-ROM, a DVD-ROM, an optical disk, a magnetic tape, a solid state storage device, a flash drive, and a signal. Storage 680 may store, for example, initial imaging geometry parameters, radiation treatment plans, biological effect models, radiation distribution models, projection images, software applications to calibrate linear accelerator 605 and/or to provide burst mode radiation treatment, and other data used to perform burst mode radiation treatment.

Operator console 660 may be located apart from linear accelerator 605, such as in a different room, in order to protect its operator from radiation. For example, linear accelerator 605 may be located in a heavily shielded room, such as a concrete vault, which shields the operator from radiation generated by accelerator 605.

Each of the devices shown in FIG. 6 may include fewer or more elements than those shown and are not limited to the devices shown in FIG. 6.

Figure 7:
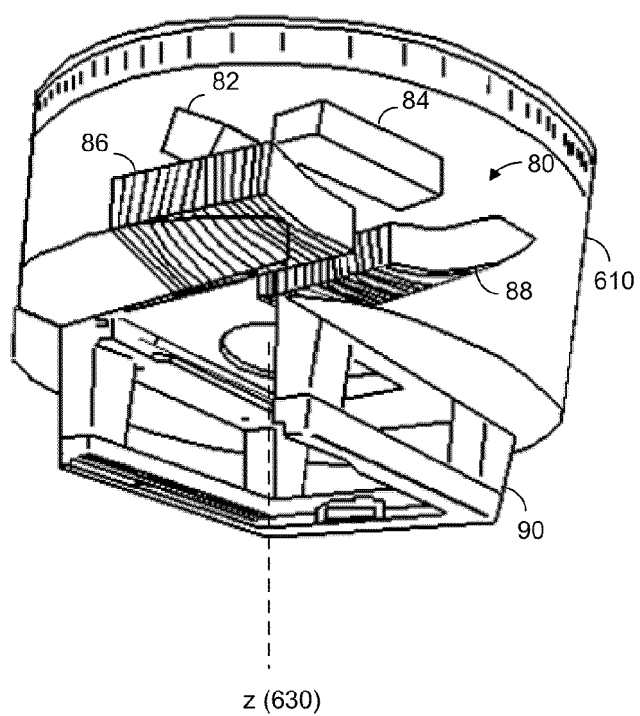
FIG. 7 is a depiction of a beam shaping device in accordance with some embodiments.

FIG. 7 illustrates treatment head 610 according to some embodiments. Treatment head 610 includes a beam shaping device, collimator 80, that may be used to shape a radiation beam to conform to an aperture specified by a treatment plan. Collimator 80 includes a pair of jaws (Y-jaws) 82 and 84 and a pair of jaws (X-jaws) 86 and 88. The positioning of X-jaws 86 and 88 and Y-jaws 82 and 84 determines a size and shape of an opening (i.e, a field of view) through which a radiation beam may pass along axis 630.

Each pair of jaws 86/88 and 82/84 is rotatable about axis 130. As depicted in FIG. 2, X-jaws 86 and 88 may be formed of a plurality of individual elements. These individual elements may be movable along a path intersecting axis 630. Movement of each element may be individually controllable to generate a wide variety of aperture shapes.

Treatment head 610 also includes accessory tray 90. Accessory tray 90 may be configured to receive and securely hold attachments used during the course of treatment planning and treatment (such as, for example, reticles, wedges, or the like). According to some embodiments, treatment head 610 is rotatable to rotate collimator 80 and accessory tray 90 around axis 630 while maintaining the physical relationships between X-jaws 86 and 88, Y-jaws 82 and 84, and accessory tray 90.

In some embodiments, radiotherapy planning for burst mode radiation treatment herein includes moving components of the radiotherapy system components (e.g., a gantry, a support table or couch, etc.). In some aspects, at least one moveable component or axis may be moved during the delivery of the burst mode radiation. Such moving axis are referred to herein as a dynamic axis since the axis may be continually moving.

Figure 8:
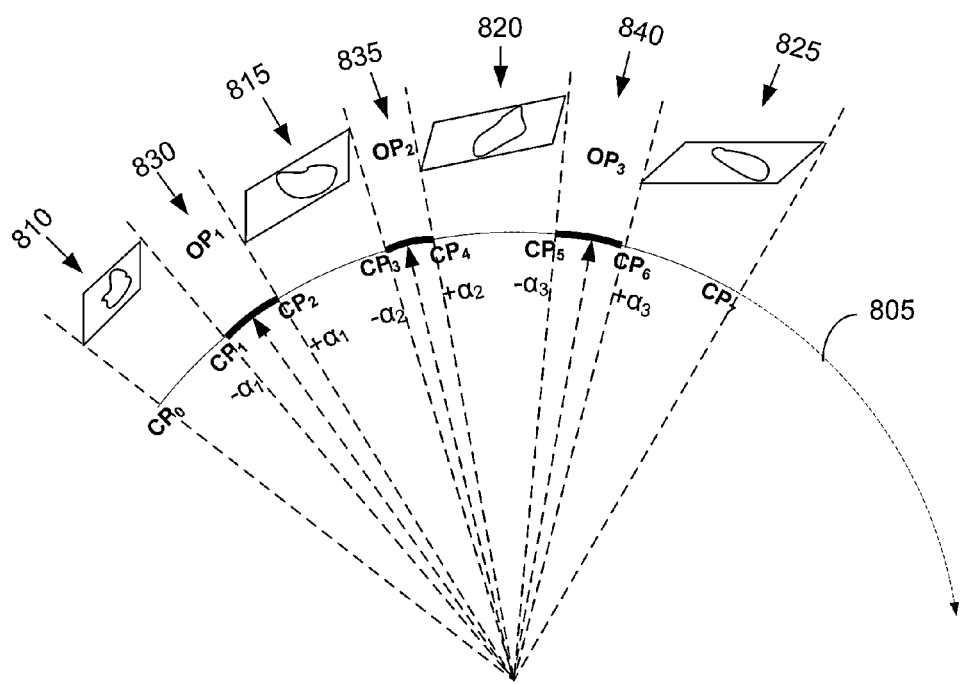
FIG. 8 is a depiction of some aspects of dynamic burst mode radiation dose delivery according to some embodiments herein.

FIG. 8 is an illustrative depiction of some aspects of radiation dose delivery according to some embodiments. More particularly, FIG. 8 illustrates various aspects of a treatment plan that may be used for delivery of burst mode radiation treatment herein.

Arc 805 represents a path gantry 615 may traverse as the gantry rotates about a patient. In the example of FIG. 8, the gantry is the moveable or dynamic axis. Other components or a combination of components (support table 645, imaging device support 640, patient 650, etc.) may be dynamically moved. In some aspects, treatment head 610 may deliver radiation to a patient area or volume of the patient, in accordance with a burst mode treatment plan, as gantry 615 rotates about the patient. In some embodiments, a burst mode treatment plan devised for treating patient 650 by radiation delivered by radiotherapy system 600 specifies a finite number of discrete control points (CPs) on arc 805. Burst mode radiation treatment scheme 800 includes a plurality of representative CPs—CP0, CP1, CP3, CP4, CP5, CP6, and CP7. Since gantry 615 continuously moves through arc 805 according to some embodiments herein, gantry 615 moves through the CPs without stopping at the CPs.

The burst mode treatment plan for treating patient 650 by burst mode radiation delivered by radiotherapy system 600 also specifies a finite number of discrete optimization points (OPs) on arc 805. Burst mode radiation treatment scheme 800 includes a plurality of representative OPs, e.g., OP1 at 830, OP2 at 835, and OP3 at 840. In some embodiments, each OP represents a treatment gantry angle at which a prescribed dose amount of radiation is to be delivered to the patient area, as specified by a burst mode treatment plan. Since gantry 615 continuously moves in a rotational manner around the patient according to some embodiments herein, gantry 615 moves through the OPs without stopping at the OPs. In some aspects, the burst mode treatment radiation is delivered around each OP since gantry 615 moves continuously. Radiation dose delivery may occur around OP by delivering the burst mode radiation ($\pm\alpha$) each gantry treatment angle. This aspect of the burst mode treatment plan and radiation delivery scheme is illustrated in FIG. 8. In some embodiments, ($\pm\alpha$) may vary from OP to OP. As illustrated in FIG. 8, $OP_1$ (830) includes ($\pm\alpha_1$), $OP_2$ (835) includes ($\pm\alpha_2$), and $OP_3$ (840) includes ($\pm\alpha_3$). Due the short ON time of the radiation beam during burst mode treatment, the delivering of the burst mode radiation occurs for a very short period of time about ($\pm\alpha$) each gantry treatment angle. The period of time during which the burst mode of radiation is delivered to a target area or volume is referred to herein as a delivery period of burst mode irradiation.

In some embodiments herein, a burst mode treatment plan may be provided for irradiating patient 650 involving radiation treatment that accounts for moving aspects of the radiotherapy system 600 and patient 650. The burst mode treatment plan specifies a number of control points that describe a dose distribution in space. The burst mode treatment plan also specifies for each dose a number of prescriptions for parameters (i.e., axis) that control a position, a direction, a shape, and an intensity of a treatment radiation beam and a position of the target volume. The burst mode treatment plan prescribes parameters for one or more dynamic axes and position parameters for the one or more dynamic axis corresponding to a prescribed delivery period of burst mode irradiation. As used to herein, dynamic axes refer to the one or more axis that controls at least one of a position, a direction, a shape, and an intensity of a treatment radiation beam and a position of the target volume according to the burst mode treatment plan and the one or more dynamic axes are continually in motion, including during the irradiating of the target volume. Furthermore, static axes refers to the one or more axes that control at least one of a position, a direction, a shape, and an intensity of a treatment radiation beam and a position of the target volume according to the burst mode treatment plan and the one or more static axes are not in motion during the irradiating of the target according to the burst mode treatment plan.

In some embodiments, the burst mode treatment plan includes at least one dynamic axes, as described herein. Regarding the static parameters, the burst mode treatment plan contains only fixed point position(s) describing the static axes for when the treatment beam is ON (i.e., the static axes is still during a beam ON condition). For the dynamic parameters, the burst mode treatment plan contains multiple overlapping positions or a range of positions describing the dynamic axes for a treatment beam ON condition, as prescribed by the burst mode treatment plan.

In accordance with embodiments herein, one or more axes of motion may be specified or defined by the burst mode treatment plan. While the example of FIG. 8 discusses the movement of the gantry as one of the dynamic axes that is constantly moving, including during a treatment beam ON period, other moveable components of the radiotherapy system 600 and the patient may be controlled to move as expressed by the dynamic axes parameters. In some embodiments, a number of axes of radiotherapy system 600 may be manipulated and moved to control a position, a direction, a shape, and an intensity of a treatment beam or a position of a patient.

In some embodiments, gantry 615 may be controlled, as shown in the example of FIG. 8, to move or alter the position of a treatment beam. However, embodiments herein are not limited to movement related to the gantry. In some embodiments, support table 645 may be rotated or otherwise moved, arm 640 supporting imaging device 635 may be moved, treatment head 610, and other components of system 600 may be moved. In some embodiments, a position of patient 650 may be moved or varied.

The shape of the treatment radiation beam may be shaped by beam shaping device 80 (e.g., MLC leaves) at each OP. In some embodiments herein, beam shaping device 80 may be configured to invoke a biological effect comparable to a grid therapy when coupled with irradiating the target volume. As used herein, spatially separated radiation therapy includes grid therapy. Furthermore, in some embodiments herein beam shaping device 80 may be configured in one or more shapes, orientations, and opening sizes such that the biological effects exhibited by conventional grid therapy may be obtained by a controlled manipulation of the beam shaping device. To the extent that embodiments herein may seek to achieve radiation biological results or effects similar to or the same as provided grid therapy, the beam shaping device may be configured with any shape, orientation, and opening size that provides the similar or same biological results. Accordingly, some embodiments herein need not achieve or attempt to emulate a physical grid or other fixed pattern common to conventional grid therapy since the effects of the radiation treatment may be determining factor of consideration.

Without a need to achieve or even attempt to emulate a fixed grid or other fixed pattern of a conventional grid therapy, beam shaping device 80 may be varied in shape, orientation, and opening size to produce biological effects for spatially separated radiation therapy. Beam shaping device 80 may be varied in shape, orientation, and opening size without a constraint to mimic or otherwise emulate a physical grid or other fixed pattern common to conventional grid therapy.

In some embodiments, the configuration of beam shaping device 80 may be varied during the course of a burst mode radiation treatment session or other radiation delivery to achieve a desired biological effect. The adjustment of beam shaping device 80 to obtain the one or more shapes, sizes, and orientations that will render the desired biological results when a burst mode treatment beam is shaped by the beam shaping device and the shaped beam irradiates the target volume may be done before a particular delivery period of the radiation. For example referring to FIG. 8, beam shaping device 80 may be configured or moved during periods 810, 815, 820, and 825. However, beam shaping device 80 is still or static during the delivery periods of the burst mode radiation. For example, whereas the dynamic axis of FIG. 8 (e.g., the gantry) is continuously in motion, beam shaping device 80 is static and not moving during the delivery periods of the burst mode radiation in time intervals 830, 835, and 840 when the burst mode radiation is ON.

In some embodiments, beam shaping device 80 is static and not moving during the delivery periods of the burst mode radiation. As a consequence of the beam shaping device 80 being static and not moving during the delivery periods of the burst mode radiation, precise (or as precise as can be physically achieved) shaped fields of radiation may be delivered to a target volume. In this manner, "smearing" of the delivered radiation due to a changing beam shape caused by a varying beam shaping device may be reduced or eliminated.

The amount of dose of radiation to be delivered at each OP may be modified and/or optimized based on the number of OPs and the radiation dosage to be delivered to the patient area. The optimization may be done so that an aggregate of all OPs results in an optimum treatment plan.

In some aspects, a burst mode treatment plan incorporates the constraint that a radiotherapy device with a continually moving dynamic axis and a beam shaping device achieve certain biological effects in a target volume. Accordingly, a burst mode treatment plan herein may include configuration parameters for the beam shaping device to invoke or yield a biological effect for spatially separated radiation therapy. The configuration parameters may include a shape, an orientation, and an opening size of the beam shaping device. Furthermore, the configuration parameters may include a sequence of shapes, orientations, and opening sizes for the beam shaping device, which when applied in cooperation with the other aspects and parameters defined by the spatially separated radiation treatment plan, operate to invoke or yield the desired biological effect(s) for spatially separated radiation therapy.

In some aspects, the desired biological effects may be obtained through a variety of shapes, orientations, and opening sizes for the beam shaping device. Furthermore, the variety of shapes, orientations, and opening sizes for the beam shaping device in conjunction with prescribed radiation doses may function to provide the desired biological effects.

In some embodiments, a radiotherapy treatment planning professional may enter a radiotherapy prescription into a planning system that specifies the amount of dose radiation a targeted patient volume receives. The treatment plan may also specify a maximum dose of radiation that the organs at risk (OAR) are allowed to receive. Additional considerations and constraints of the treatment plan may also be specified or otherwise entered and included in the spatially separated radiation treatment plan planning system.

In some embodiments, a spatially separated radiation treatment plan may include one or more instructions for specifying and controlling a radiotherapy system. As such, a treatment plan may vary in complexity and include a single instruction regarding one parameter and may also include a plurality of instructions for controlling a plurality parameters.

In accordance with some aspects of the burst mode radiation treatment of targets herein, a planning system assumes the delivery of the radiation treatment is to be done by a continuously moving dynamic axis. Some of the parameters of the dynamic axis may have physical, practical, or other types of speed limitations that may be specified or otherwise accounted for in the planning system. Other operating limitations or constraints on, for example, beam shaping device 80 such as MLC leaf speed, may also be provided to the planning system. Furthermore, the prescribed dose rate and a specific period of time for delivering the treatment radiation may be provided to the burst mode treatment planning system. Based on such provided and specified information, the burst mode treatment planning system may create an optimum plan for burst mode radiation treatment using a beam shaping device to invoke a biological effect.

Referring to FIG. 8, beam shaping device may be, for example, configured between CP0 and CP1 at 810, CP2 and CP3 at 815, CP4 and CP5 at 820, and CP6 and CP7 at 825 and held static during the delivery period of the burst mode radiation. Still referring to FIG. 8, a dose of radiation treatment is delivered to a patient target volume dynamically during a burst window between CP1 and CP2 at 830, CP3 and CP4 at 835, and CP5 and CP6 at 840. The beam shaping device is held static during the burst windows.

In some embodiments, the beam shaping device in the current example reaches its desired destination position before the occurrence of a next treatment delivery period. Referring to FIG. 8, the static axis may be moved during, for example period 810, to reach their designated positions per the burst mode treatment plan before the occurrence of the next treatment delivery period 830.

Figure 9:
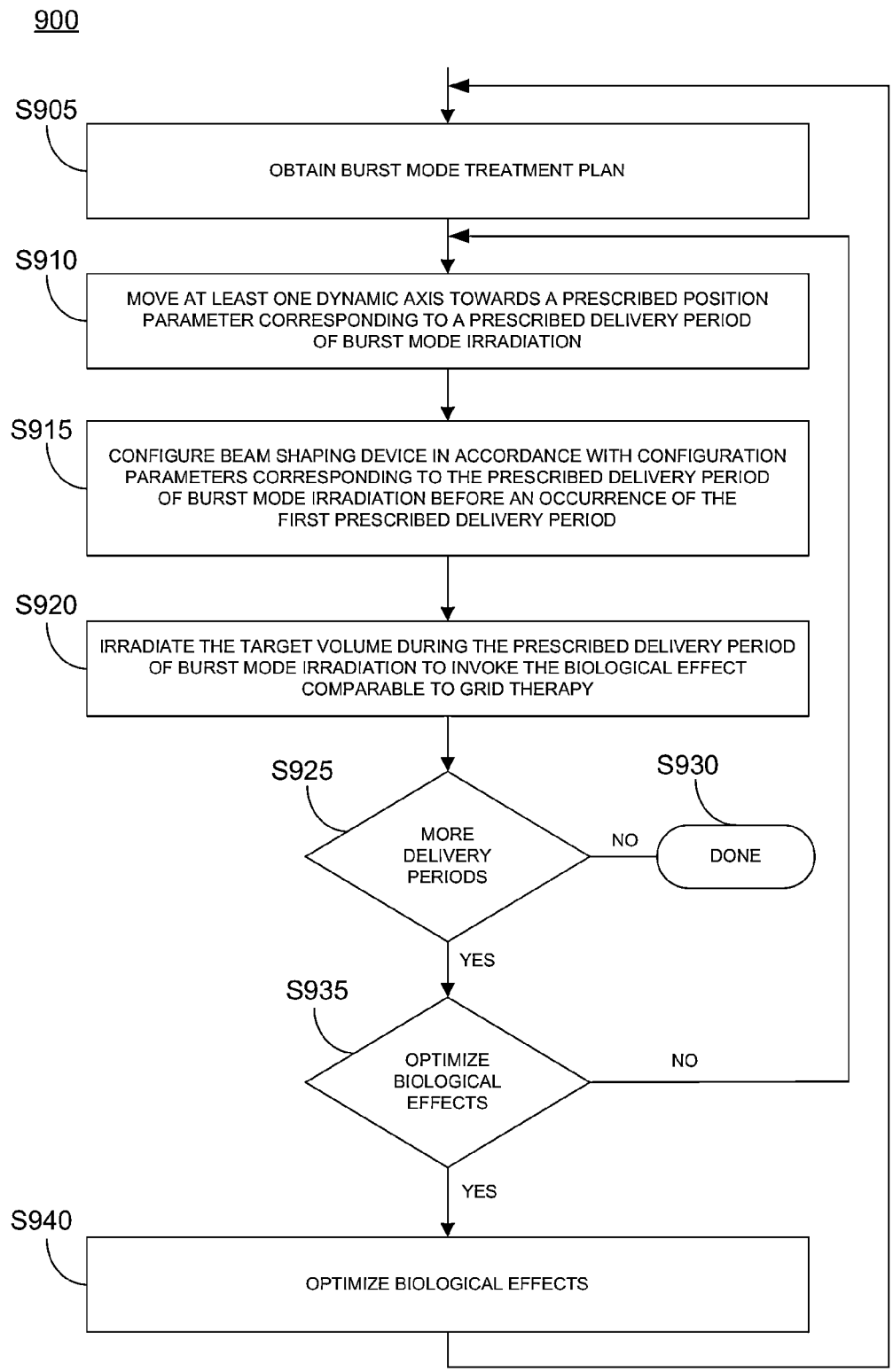
FIG. 9 is a flow diagram according to some embodiments.

FIG. 9 is a flow diagram of a process 900 to provide burst mode radiation treatment using a beam shaping device to invoke biological effects comparable to grid therapy, according to some embodiments. Process 900 and the other processes described herein may be performed using any suitable combination of hardware, software or manual means. Software embodying these processes may be stored by any medium, including a fixed disk, a floppy disk, a CD-ROM, a DVD-ROM, an optical disk, a magnetic tape, a solid state storage device, or a signal. Examples of these processes will be described below with respect to the elements of radiotherapy treatment room 900, but embodiments are not limited thereto.

In some embodiments, and prior to S905, a burst mode treatment plan may be established. At S905, an operator may obtain the treatment plan. In some embodiments, the burst mode treatment plan, or parts thereof, may be determined and established at S905. The burst mode treatment plan of S905 may include prescribing parameters for at least one dynamic axis and position parameters for the at least one dynamic axis corresponding to a prescribed delivery period of burst mode irradiation.

At S910, the dynamic axis may be moved towards a prescribed position parameter that corresponds to a prescribed delivery period of burst mode irradiation. For example, gantry 615 of the radiotherapy device may be moved towards a first prescribed delivery period for the delivery of the burst mode radiation.

Returning to FIG. 9, the target volume is irradiated with radiation during the prescribed delivery period at S920. Since the beam shaping device has been configured to invoke the desired biological effect at S915, the irradiating at S920 may result in achieving the desired biological effects. In some embodiments, the biological effects may be achieved or facilitated by a collective set of physical doses delivered in combination with the prescribed beam shaping device configurations. The collective set of different physical doses may be determined, calculated, or otherwise known to increase a probability of achieving the desired biological effect(s).

At S925, a determination may be made whether there are more prescribed delivery periods calling for the delivery of additional radiation. In the instance there are no more delivery periods prescribed by the treatment mode, process 900 may terminate at S930. In the instance there are more delivery periods for the delivery of additional radiation, process 900 proceeds to S935 where it is determined whether to optimize the biological effects. In the instance an optimization will not be performed, process 900 returns to S910.

Optimization of the biological effects may entail tuning the configuration parameters for the beam shaping device. The tuning of the configuration parameters for the beam shaping device may involve an iterative process where prior biological effects are analyzed and adjustments are made to the configuration parameters for the beam shaping device in an effort to increase the biological effects realized by the burst mode radiation treatment herein. Upon completion of the optimization at S940, the process flow returns to S905. The treatment plan at S905 may be updated to include the biological effect optimization(s) from S940

The several embodiments described herein are solely for the purpose of illustration. Therefore, persons in the art will recognize from this description that other embodiments may be practiced with various modifications and alterations.

What is claimed is:

1. A computer-implemented method, the method comprising:
    dividing a representation of a target volume into an array of sub-volumes;
    defining, for each sub-volume, a high dose volume to which a high dose of radiation is to be delivered;
    defining, for each sub-volume, a plurality of sampling volumes, the sampling volumes being smaller than the high dose volume of each sub-volume;
    delivering an estimated dose of radiation to each sub-volume;
    determining, by a processor, whether the dose of radiation delivered to each high dose volume is at least a minimum threshold dose, and that the radiation delivered to each of the sub-volumes, spatially outside of the high dose volume, within the plurality of sampling volumes, is at least a minimum difference less than the radiation delivered to the high dose volume;
    adjusting, by the processor, the estimated dose of radiation delivered to each sub-volume so that each high dose volume receives at least a minimum threshold dose, and the radiation delivered to each of the sub-volumes spatially outside of the high dose volume within the plurality of sampling volumes is at least a minimum difference less than the radiation delivered to the high dose volume; and
    developing a radiation treatment plan, including the adjusted dose, to invoke a biological effect of spatially separated radiation.

2. The method of claim 1, wherein the high dose volume is substantially located in a central portion of each sub-volume.

3. The method of claim 1, wherein the minimum threshold dose of radiation is about 70% to 90% of an estimated maximum dose of radiation.

4. The method of claim 1, wherein the sub-volumes are spaced apart within a pre-determined minimum distance of about 1 centimeter and a maximum distance of about 5 centimeters from each other.

5. The method of claim 1, wherein the minimum difference is about 50% to 60% below the dose of radiation directed to each sub-volume.

6. The method of claim 1, wherein the adjusting includes lowering the estimated dose directed to at least some of the sub-volumes.

7. The method of claim 1, wherein the high dose volume is about 5% to 20% of each sub-volume.

8. The method of claim 1, wherein the adjusting further comprises altering a spatial relationship between the high dose volumes, the sampling volumes, and the sub-volumes.

9. The method of claim 1, wherein each sampling volume is about 1% to 10% of the sub-volume.

10. The method of claim 1, further comprising:
    administering the radiation treatment plan, including the adjusted dose, to invoke the biological effect of spatially separated radiation by delivering a radiotherapy treatment to the target volume by a radiotherapy device, wherein the target volume is within a patient.

11. The method of claim 10, further comprising:
    obtaining the treatment plan to be administered, the treatment plan prescribing configuration parameters for a beam shaping device of the radiotherapy device and prescribed doses to invoke the biological effect of spatially separated radiation;
    moving the radiotherapy device towards a first prescribed position for irradiation of the target volume;
    configuring the beam shaping device in accordance with the configuration parameters corresponding to the first prescribed position; and
    irradiating the target volume with the radiotherapy device at the first prescribed position to invoke the biological effect of spatially separated radiation.

12. The method of claim 11, wherein the treatment plan is a burst mode treatment plan.

13. The method of claim 12, wherein:
    at least one dynamic axis of the radiotherapy device is continually in motion during a treatment session, including during the irradiating of the target volume; and
    the beam shaping device is not in motion during the irradiating of the target volume.

* * * * *